United States Patent [19]

Oghoshi et al.

[11] 3,997,576
[45] Dec. 14, 1976

[54] METHOD FOR PREPARATION OF α-SULFOFATTY ACID ESTER

[75] Inventors: Toshiaki Oghoshi, Funabashi; Yukio Kusumi, Chiba, both of Japan

[73] Assignee: Lion Fat & Oil Co., Ltd., Tokyo, Japan

[22] Filed: Apr. 17, 1975

[21] Appl. No.: 568,851

[30] Foreign Application Priority Data

Apr. 22, 1974 Japan .................. 49-44456

[52] U.S. Cl. .............. 260/410.9 R; 252/557; 260/400
[51] Int. Cl.² ................................. C07C 143/90
[58] Field of Search ............ 260/410.9 R, 400

[56] References Cited

FOREIGN PATENTS OR APPLICATIONS

| | | | |
|---|---|---|---|
| 1,468,032 | 1/1969 | Germany | 260/400 |
| 1,418,887 | 5/1971 | Germany | 260/400 |
| 1,178,845 | 10/1964 | Germany | 260/400 |

OTHER PUBLICATIONS

Stein, W. et al. "Preparation of Esters of α–Sulfo–Fatty Acids" Fette–Seifen–Anstrichmittel 72 (11) (1970) pp. 956–959.

*Primary Examiner*—Helen M. McCarthy
*Attorney, Agent, or Firm*—Woodhams, Blanchard and Flynn

[57] ABSTRACT

An α-sulfofatty acid ester useful as the intermediate of active ingredient for detergent can be prepared by making a saturated fatty acid having 8 to 20 carbon atoms react with a mixture gas consisting of an inert gas and $SO_3$ in the presence of an aliphatic alcohol having 1 to 4 carbon atoms.

6 Claims, No Drawings

METHOD FOR PREPARATION OF α-SULFOFATTY ACID ESTER

BACKGROUND OF THE INVENTION

The present invention relates to a method of preparing an α-sulfofatty acid ester useful as the intermediate of active ingredient for detergent, and it relates particularly to a method of directly obtaining an α-sulfofatty acid ester by making a fatty acid react with $SO_3$ in the presence of an alcohol.

The art of preparing an α-sulfofatty acid ester by sulfonating a fatty acid ester by means of sulfur trioxide is well known. However, this conventional method is more or less accompanied with the hydrolysis of the ester at the time of sulfonation and besides the speed of sulfonation reaction therein is low, so that it necessitates not only the application of excess sulfur trioxide but also the aging for a substantial time subsequent to the sulfonation.

As an alternative to the foregoing method, there is also known a method of preparing an α-sulfofatty acid ester which comprises sulfonating a fatty acid in the first place and then esterifying the sulfonation product. This method admittedly has an advantage that the speed of sulfonation reaction therein is high, but it is defective in that the viscosity of the reaction product increases remarkably with the progress of said sulfonation reaction.

By the way, an α-sulfofatty acid ester becomes an active ingredient for detergent subject to neutralization of the sulfonic acid group thereof to turn into an alkali salt. Meanwhile, an α-sulfofatty acid prepared by either one of the above two methods is colored with the by-products arising from the sulfonation reaction, and accordingly, it is normally required to subject said α-sulfofatty acid ester to the bleaching treatment prior to subjecting it to the neutralization treatment. This bleaching treatment is generally performed by the use of hydrogen peroxide, and therefore, there is a fear of a part of the ester linkage being hydrolyzed at the time of said treatment. This fear is aggravated when the degree of coloring of α-sulfofatty acid ester is remarkable as it necessitates application of more severe conditions in performing the bleaching treatment. An hydrolysis of the ester at the time of the bleaching treatment is undesirable for the reason that it will increase the by-product dialkali metal salt of α-sulfofatty acid, which is inferior in water-solubility and detergency, at the time of neutralization treatment subsequent thereto.

Said dialkali metal salt of α-sulfofatty acid has in fact no serious influence on the water-solubility and detergency as a whole when the amount thereof is little relative to the amount of alkali metal salt of α-sulfofatty acid ester. In this sense, the method disclosed in DT-OS 1418887, which aims to increase the yield of active ingredient for detergent through the procedure comprising subjecting a fatty acid ester to sulfonation reaction, subsequently sulfonating an aliphatic higher alcohol with excess $SO_3$ present in the reaction product and neutralizing thereafter, is admittedly an effective means for relatively reducing the influence of dialkali metal salt of α-sulfofatty acid which is undesirable as the active ingredient for detergent.

Accordingly, it is a must to obtain an α-sulfofatty acid ester useful as the intermediate of active ingredient for detergent at the possibly higher yield and in the state of being minimized in coloring for relatively reducing the ratio of α-sulfofatty acid to be inevitably brought about as a by-product in the subsequent bleaching process to α-sulfofatty acid ester.

SUMMARY OF THE INVENTION

The present invention is intended to provide a method of preparing an α-sulfofatty acid ester which well satisfies the above discussed requirement. That is, the present invention renders successful synthesis of an α-sulfofatty acid ester minimized in coloring at a high yield by making a saturated fatty acid having 8 to 20 carbon atoms react with an inert gas-$SO_3$ mixture gas containing 1.2 to 4 moles of sulfur trioxide per mole of said saturated fatty acid in the presence of 1 to 2.2 moles of an aliphatic alcohol having 1 to 4 carbon atoms per mole of the saturated fatty acid.

The reason why an α-sulfofatty acid ester minimized in coloring can be obtained at a high yield according to the present invention is yet to be clarified, but it is probably attributable to the fact that a part of $SO_3$ employed as the sulfonation agent is also concerned in the esterification reaction. In other words, it is presumable that, in the present invention, not only $SO_3$ acts as a dehydrating agent for water coming out as a by-product at the time of esterification reaction but also the sulfuric acid produced through reaction between $SO_3$ and water functions as a catalyst and/or dehydrating agent in the esterification reaction, and consequently α-sulfofatty acid ester can be produced at a high yield.

DESCRIPTION OF THE PREFERRED EMBODIMENTS

The material fatty acid applicable in the present invention is a saturated fatty acid having 8 to 20 carbon atoms, such as lauric acid, myristic acid, palmitic acid, stearic acid, hydrogenated coco fatty acid, hydrogenated palm fatty acid, hydrogenated tallow fatty acid, and straight-chain or branchedchain fatty acid synthesized from α-olefin and carbon monoxide. In this context, in the case where a fatty acid mixture is applied as the material, the iodine number thereof is preferably less than 1.

As the aliphatic alcohol for use in the present invention, methanol, ethanol, n-propanol, iso-propanol, n-butanol, isobutanol, etc. are applicable, and the amount of said aliphatic alcohol to be employed is selected from the range of from 1 to 2.2 moles — preferably from 1.2 to 2.0 moles — per mole of the aforesaid saturated fatty acid: in the case where the amount of alcohol employed is less than the foregoing range, a satisfactory progress of the esterification reaction cannot be expected and accordingly an α-sulfofatty acid ester cannot be produced at a high yield, while employment of said alcohol in an amount exceeding said range is uneconomical and is undesirable as it gives rise to impurities as by-product. In this connection, an alcohol having more than 5 carbon atoms is not employed in the present invention as it is inferior in reactivity and causes impurities as by-product.

In practicing the present invention, the whole amount of said aliphatic alcohol having 1 to 4 carbon atoms as required may be previously mixed with the material fatty acid, but it also will do to apply the process that the material fatty acid is first subjected to sulfonation without mixing with said alcohol and the alcohol is gradually added to the reaction zone prior to completion of the sulfonation reaction, or the process that a part of the alcohol is previously mixed with the material fatty acid and, while effecting sulfonation thereof, the remainder of the alcohol is gradually added prior to completion of the sulfonation reaction.

$SO_3$ gas is normally employed upon diluting it with an inert gas such as air and nitrogen to the extent of 3 to 20 vol.%, but the amount of $SO_3$ should be in the range of from 1.2 to 4 moles — preferably from 1.5 to 3.5 moles — per mole of the material fatty acid: in the case where the amount. $SO_3$ is less than 1.2 mole, a satisfactory progress of the sulfonation reaction cannot be expected, while the case where it is more than 4 moles, the sulfonation reaction is much precipitated, causing a local overheating, whereby the coloring of the reaction product is aggravated. $SO_3$ gas for use in the present invention may be one obtained by gasifying a liquid $SO_3$ or one obtained by burning sulfur.

Referring to the reaction conditions, the temperature for reaction is set at a temperature sufficient for maintaining the fluidity of the material fatty acid and alcohol and is generally selected from the range of from 50° to 100° C — preferably from 60° to 90° C: in the case where it exceeds 100° C, the coloring of the reaction product becomes conspicuous, so that it is undesirable, while in the case where it is less than 50° C, the progress of reaction is slow and takes a long time, so that it is also undesirable. As to the time for reaction, strictly speaking, it varies with the batch-wise operation and the continuous operation of the reaction: in the case of the batch-wise operation, it is desirable to be in the range of from 30 to 120 minutes, and to effect reaction with $SO_3$ for more than 120 minutes will bring about a terrible coloring of the reaction product, while in the case of the continuous operation, it is desirable to provide the aging process for the effluent from the reaction zone.

As elucidated in the foregoing, the present invention renders it possible to prepare an $\alpha$-sulfofatty acid ester as minimized in coloring at a high yield by directly employing a fatty acid as the starting material. Accordingly, an $\alpha$-sulfofatty acid ester obtained in the present invention is to serve as an active ingredient for detergent upon undergoing the bleaching and neutralization treatments as usual, but this active ingredient can be made into a detergent composite by compounding with other surface active agent, inorganic or organic builder and appropriate detergent assistant as occasion demands.

Hereunder will be further elucidated the concrete effect of the present invention with reference to embodiments thereof.

EXAMPLE 1

120 g (1.5 mole) of sulfur trioxide gas diluted to have a concentration of 5 vol.% were introduced into 276 g (1 mole; iodine number = 0.23) of hydrogenated tallow fatty acid at a reaction temperature in the range of from 70° to 80° C over 60 minutes. 30 minutes after starting said introduction, 64 g (2 moles) of methyl alcohol were added over 15 minutes. Upon completion of the introduction, the resulting mixture was neutralized with 4% aqueous solution of caustic soda, and then the properties of the thus neutralized mixture were examined. As a result, the rate of sulfonation of the reaction product was 85.1% and the rate of esterification thereof was 99.0%. The color tone of 0.5% aqueous solution of said product in terms of the absorbance-log T as measured with a spectrophotometer under the condition of the glass cell being 10 mm, the width of slit being 0.05 mm and the water-length being 420 m$\mu$ was 0.65. (The same conditions for measurement of the color tone as above will apply to the succeeding examples.) Further, when the product was subjected to the bleaching treatment with sodium hypochlorite in an amount of 4% relative to the activator (sulfonation product), the rate of esterification was 96.1%, and the color tone of 5% aqueous solution of the thus treated product was 0.57.

The foregoing result verifies that a relatively high rate of sulfonation and a high rate of esterification can be obtained in the sulfonation reaction, and as the hydrolysis of ester during the bleaching treatment is slight, there can be obtained an $\alpha$-sulfofatty acid ester having desirable properties.

COMPARATIVE EXAMPLE 1

120 g (1.5 mole) of sulfur trioxide gas diluted to have a concentration of 5 vol.% were introduced into 276 g (1 mole; iodine number = 0.23) of hydrogenated tallow fatty acid at a reaction temperature in the range of from 70° to 80° C over 60 minutes. After 60 minutes' esterification at 80° C by adding 64 g of methyl alcohol subsequent to said introduction, the resulting mixture was neutralized with 4% aqueous solution of caustic soda, and then the properties of the thus neutralized mixture were examined. As a result, the rate of sulfonation of the reaction product was 82.4%, the rate of esterification thereof was 96.5%, and the color tone of 0.5% aqueous solution of same was 2.0. Further, when the product was subjected to the bleaching treatment with sodium hypochlorite in an amount of 4% relative to the activator (sulfonation product), the rate of esterification was 93.8%, and the color tone of 5%) aqueous solution of the thus treated product was 1.80, while the case where the product was subjected to the bleaching treatment with sodium hypochlorite in an amount of 8% relative to the activator (sulfonation product), the rate of esterification was 89.3%, and the color tone of 5% aqueous solution of the thus treated product was 1.37.

The foregoing result verifies that the product from esterification effected after sulfonation is inferior to the product of Example 1 in respect of the rate of sulfonation, the rate of esterification and the degree of coloring, and especially its coloring is remarkable. An attempt to promote the bleach would result in a substantial deterioration of the properties of the product $\alpha$-sulfofatty acid ester due to hydrolysis of the ester linkage thereof.

EXAMPLE 2

160 g (2 moles) of sulfur trioxide gas diluted to have a concentration of 5 vol.% were introduced into a mixture consisting of 213 g (1 mole; iodine number = 0.32) of hydrogenated coco fatty acid and 102 g (1.7 mole) of iso-propyl alcohol at a reaction temperature in the range of from 50° to 80° C over 80 minutes. After completion of said introduction, the resulting mixture was neutralized with 4% aqueous solution of caustic soda, and then the properties of the thus neutralized mixture were examined. As a result, the rate of sulfonation of the reaction product was 92.5%, the rate of esterification thereof ws 95.2%, and the color tone of 0.5% aqueous solution of same was 0.74. Further, when the product was subjected to the bleaching treatment with sodium hypochlorite in an amount of 4% relative to the activator (sulfonation product), the rate of esterification was 93.5% and the color tone of 5% aqueous solution of the thus treated prduct was 0.70.

EXAMPLE 3

240 g (3 moles) of sulfuric anhydride diluted to have a concentration of 7 vol.% were introduced into a mixture consisting of 285 g (1 mole) of stearic acid and 23 g (0.5 mole) of ethanol at a reaction temperature in the range of from 70° to 85° C over 90 minutes. 40 minutes after starting said introduction, 69 g (1.5 mole) of ethanol were added to the resulting mixture. Upon completion of the introduction, the mixture was neutralized with 4% aqueous solution of caustic soda, and then the properties of the thus neutralized mixture were examined. As a result, the rate of sulfonation of the reaction product was 91.2%, the rate of esterification thereof was 96.4%, and the color tone of 0.5% aqueous solution of same was 0.80. Further, when the product was subjected to the bleaching treatment with sodium hypochlorite in amount of 4% relative to the activator (sulfonation product), the rate of esterification was 93.6% and the color tone of 5% aqueous solution of the thus treated product was 0.68.

EXAMPLE 4

144 g.(1.8 mole) of sulfur trioxide gas diluted to have a concentration of 5 vol.% and 108 g (1.8 mole) of iso-propyl alcohol were simultaneously introduced into 270 g (1 mole; rate of straight-chain/branched-chain = 76.7/23.3; iodine number = 0.51) of a fatty acid obtained through hydrocarboxylation of n-hexadecene-1 at a reaction temperature in the range of from 65° to 90° over 60 minutes. Upon completion of the introduction, the resulting mixture was neutralized with 4% aqueous solution of caustic soda, and then the properties of the thus neutralized mixture were examined. As a result, the rate of sulfonation of the reaction product was 82.3%, the rate of esterification thereof was 94.4%, and the color tone of 0.5% aqueous solution of same was 0.74. Further, when the product was subjected to the bleaching treatment with sodium hypochlorite in an amount of 4% relative to the activator (sulfonation product), the rate of esterification was 92.1%, and the color tone of 5% aqueous solution of the thus treated product was 0.66.

EXAMPLE 5

120 g (1.5 mole) of sulfur trioxide gas diluted to have a concentration of 5 vol.% were introduced into 200 g (1 mole) of lauric acid at a reaction temperature in the range of from 70° to 80° C over 60 minutes. 20 minutes after starting said introduction, 48 g (1.5 mole) of methyl alcohol were added over 30 minutes. Upon completion of the introduction, the resulting mixture was neutralized with 4% aqueous solution of caustic soda, and then the properties of the thus neutralized mixture were examined. As a result, the rate of sulfonation of the reaction product was 83.6%, the rate of esterification thereof was 91.8%, and the color tone of 0.5% aqueous solution of same was 0.47. Further, when the product was subjected to the bleaching treatment with sodium hypochlorite in an amount of 4% relative to the activator (sulfonation product), the rate of esterification was 87.2% and the color tone of 5% aqueous solution of the thus bleached product was 0.39.

What is claimed is:

1. A method of preparing an α-sulfofatty acid ester, which comprises the process of making a saturated fatty acid having 8 to 20 carbon atoms react with a gaseous mixture of an inert gas and $SO_3$ containing 1.2 to 4 moles of sulfur trioxide per mole of said saturated fatty acid in the presence of 1 to 2.2 moles of an aliphatic alcohol having 1 to 4 carbon atoms per mole of said saturated fatty acid.

2. A method according to claim 1, wherein said reaction is effected under the conditions for reaction that the temperature for reaction being in the range of from 50° to 100° C. and the time for reaction being in the range of from 30 minutes to 120 minutes.

3. A method according to claim 1, wherein the whole amount of aliphatic alcohol defined therein is mixed with said saturated fatty acid, and into the resulting mixture is introduced said gaseous mixture.

4. A method according to claim 1, wherein a part of the amount of said aliphatic alcohol defined therein is first mixed with said saturated fatty acid, and while introducing said gaseous mixture into the resulting mixture, the remainder of the aliphatic alcohol is gradually added thereto.

5. A method according to claim 1, wherein the whole amount of said aliphatic alcohol defined therein is gradually added to said saturated fatty acid while introducing said gaseous mixture into the saturated fatty acid.

6. A method according to claim 1, wherein said saturated fatty acid is selected from the group consisting of lauric acid, myristic acid, plamitic acid, stearic acid, hydrogenated coco fatty acid, hydrogenated palm fatty acid, hydrogenated tallow fatty acid, straight-chain or branched-chain fatty acid synthesized from α-olefin and carbon monoxide, and mixtures of these substances, and said aliphatic alcohol is selected from the group consisting of methyl alcohol, ethyl alcohol, propyl alcohol, iso-propyl alcohol, butyl alcohol, iso-butyl alcohol, and mixtures of these alcohols.

* * * * *